(12) United States Patent
Fan

(10) Patent No.: US 8,143,471 B2
(45) Date of Patent: Mar. 27, 2012

(54) ELECTROCHEMICAL CAPACITIVE CONCENTRATION AND DEACTIVATION OF ACTINIDE NUCLEAR MATERIALS

(75) Inventor: Qinbai Fan, Chicago, IL (US)

(73) Assignee: Gas Technology Institute, Des Plaines, IL (US)

( * ) Notice: Subject to any disclaimer, the term of this patent is extended or adjusted under 35 U.S.C. 154(b) by 974 days.

(21) Appl. No.: 11/497,092

(22) Filed: Aug. 1, 2006

(65) Prior Publication Data
US 2007/0246367 A1   Oct. 25, 2007

Related U.S. Application Data

(60) Provisional application No. 60/794,287, filed on Apr. 21, 2006.

(51) Int. Cl.
*A42D 3/00* (2006.01)
*A42D 3/10* (2006.01)
*A42D 3/115* (2006.01)
*B01D 17/06* (2006.01)
*B23H 3/04* (2006.01)

(52) U.S. Cl. ........ 588/301; 588/300; 588/303; 204/554; 204/290.02

(58) Field of Classification Search .......... None
See application file for complete search history.

(56) References Cited

U.S. PATENT DOCUMENTS

| | | | |
|---|---|---|---|
| 3,755,114 A * | 8/1973 | Tarjanyi et al. ............... | 588/302 |
| 5,527,643 A | 6/1996 | Sonobe et al. | |
| 5,582,706 A | 12/1996 | Grantham et al. | |
| 5,858,199 A * | 1/1999 | Hanak ............................ | 205/687 |
| 6,299,778 B1 * | 10/2001 | Penth et al. ................... | 210/650 |
| 6,309,532 B1 * | 10/2001 | Tran et al. ..................... | 205/687 |
| 6,610,414 B2 * | 8/2003 | Goyal et al. ................... | 428/551 |
| 6,824,662 B2 | 11/2004 | Liang et al. | |
| 6,929,735 B2 | 8/2005 | Prohaska et al. | |
| 2001/0014405 A1 * | 8/2001 | Yuzawa et al. ................ | 428/568 |
| 2002/0172869 A1 * | 11/2002 | Kudo et al. .................... | 429/232 |
| 2004/0007466 A1 | 1/2004 | Seo et al. | |
| 2005/0131163 A1 * | 6/2005 | Rhine et al. ................... | 525/420 |

(Continued)

FOREIGN PATENT DOCUMENTS

CN            150874        *  6/2004

(Continued)

OTHER PUBLICATIONS

Farmer, Joseph C. et al., "Capacitive Deionization of NaCI and NaNO3 Solutions with Carbon Aerogel Electrodes", *J. Electrochem. Soc.*, 143, 159-169 (1996).

(Continued)

*Primary Examiner* — Melvin Mayes
*Assistant Examiner* — Sheng H Davis
(74) *Attorney, Agent, or Firm* — Mark E. Fejer

(57) ABSTRACT

An apparatus for concentration and deactivation of actinide nuclear materials having a pair of spaced apart electrodes made of a composite material including at least one oxide, at least one carbon-containing material and lead, a nuclear waste water stream flowing between the electrodes, and a DC power supply operably connected with the electrodes. When a voltage is applied to the spaced apart electrodes, nuclear cations in the nuclear waste water stream are attracted to one of the electrodes and anions in the nuclear waste water stream are attracted to the other of the electrodes, forming a substantially deionized water stream and a concentrated nuclear waste stream.

7 Claims, 4 Drawing Sheets

U.S. PATENT DOCUMENTS

2006/0016689 A1 * 1/2006 Carson et al. ............... 205/43
2006/0091079 A1 * 5/2006 Meng et al. ............... 210/688

FOREIGN PATENT DOCUMENTS

| | | | |
|---|---|---|---|
| FR | 02774100 | * | 7/1999 |
| JP | 49072180 | * | 7/1974 |
| JP | 59136189 | * | 8/1984 |
| JP | 61045998 | * | 3/1986 |

OTHER PUBLICATIONS

Morris, David E., "Aqueous Electrochemical Mechanisms in Actinide Residue Processing", Final Report to Department of Energy, LANL Project 59967, Sep. 30, 2000.

* cited by examiner

ELECTROCHEMICAL CAPACITIVE CONCENTRATION AND DEACTIVATION OF ACTINIDE NUCLEAR MATERIALS

BACKGROUND OF THE INVENTION

1. Field of the Invention

This invention relates to the concentration and deactivation of actinide-containing materials from nuclear fuel cycles. More particularly, this invention relates to an electrochemical apparatus for concentrating and deactivating actinide-containing materials from nuclear fuel cycles. This invention further relates to a method for concentrating and deactivating actinide-containing materials from nuclear fuel cycles.

2. Description of Related Art

The processing of nuclear waste residue waste streams to reduce radio nuclide activity levels and matrix volume is a significant challenge which must be overcome to achieve nuclear stabilization and volume reduction so that geologic repositories will provide adequate storage volume. Although these nuclear waste residues contain fairly stable oxide forms, they are very dilute.

Residues containing actinides include graphite, pyrochemical salts, combustibles, incinerator ash, ceramic crucibles, plastic filters, and sand/slag crucibles. Currently, most of these wastes are stored and buried. It is known, however, that incinerator ash, sand and related materials can be treated with oxidative catalysts to reduce plutonium concentrations to a very low level.

Some oxides, such as $TiO_2$ and $SiO_2$, have been shown to attract actinide cations. See Morris, D. E., "Aqueous Electrochemical Mechanisms in Actinide Residue Processing", Final Report to U.S. Department of Energy, LANL Project 59967, Sep. 30, 2000. In this report, a mediated electrochemical oxidation/reduction process (MEO/R) was used to achieve nuclear stabilization and volume reduction. In particular, sorption reactions of $UO_2^{2+}$ and $Eu^{3+}$ on $SiO_2$ and $TiO_2$ and several aluminosilicate minerals were investigated. In this electrochemical process, anion clusters of $SiO_2$ and $TiO_2$ are formed in an aqueous solution which adsorb the nuclear cations to form precipitates. Thus, the nuclear wastes are entrained in the metal oxides and form stable suspensions with high solids concentrations. However, disadvantageously, this method requires the use of a fine powder capture process and it is difficult to separate the metal oxide and the nuclear concentrates.

Known water purification methods include distillation, ion-exchange, carbon adsorption, filtration, ultrafiltration, reverse osmosis, electrodeionization, ultraviolet radiation and combinations thereof. However, each of these methods has shortcomings. Distillation cannot remove some volatile organics and it consumes large amounts of energy. In the ion-exchange process, water is percolated through bead-like spherical resin materials. However, the resin materials need to be regenerated and changed frequently. In addition, this method does not effectively remove particles, pyrogens, or bacteria. The carbon adsorption process can remove dissolved organics and chlorine with long life and high capacity; however, fine carbon particles are generated during the process due to corrosion. Micropore membrane filtration, a high cost process, removes all particles and microorganisms greater than the pore size of the membrane; however, it cannot remove dissolved inorganics, pyrogens or colloids. The ultrafilter is a tough, thin, selectively permeable membrane that retains most macromolecules above a certain size, including colloids, microorganisms, and pyrogens; however, it will not remove dissolved organics. Reverse osmosis is the most economical method for removing 90 to 99% of all contaminants. Reverse osmosis membranes are capable of rejecting all particles, bacteria, and organics; however, the flow rate or productivity is low. Electrodeionization is a combination of electrodialysis and ion-exchange, resulting in a process which effectively deionizes water while the ion-exchange resins are continuously regenerated by the electric current; however, this method requires pre-purification to remove powders and ash materials.

FIG. 1 is a diagram showing a capacitive deionization process with carbon aerogel electrodes. In this process, salt water is introduced into the cell, the negative electrode (anode) 11 adsorbs positive ions 13 and the positive electrode (cathode) 12 adsorbs negative ions 14. When the cell is charged, pure water is obtained, and when the cell is discharged, concentrated salt water is removed. To achieve this result, pulsed electrical power at voltages from 1.2V to 0V is used for different time periods depending on the concentration of the salt water and the activity of the activated carbon. The more accessible surface area the electrode has, the more ions that can be stored. The main problem with this method is that the electrosorption capacity (salt removal) decreases with cycle life. Most of the capacity loss can be recovered by periodic reversing of the electrode polarization. However, the interface between the active carbon and the aerogel diminishes, reducing the actual electrode active area. That is, the carbon particles will no longer contact each other and, ultimately, will leach out.

SUMMARY OF THE INVENTION

It is, thus, one object of this invention to provide a method and apparatus for concentrating and deactivating actinide materials.

It is one object of this invention to provide a method and apparatus for concentrating and deactivating actinide materials to produce deionized water which addresses the problems encountered with conventional capacitive deionization (CDI) including carbon gel electrode performance decay, susceptibility of the polymer binder employed in the carbon electrodes to chemical and electrochemical attacks, carbon corrosion and electrode erosion, and the adsorption of soluble organic matter which reduces sites available for ion interactions.

It is yet a further object of this invention to provide a method and apparatus for concentrating and deactivating actinide materials which eliminates the powder mixture reaction and filtration encountered in the MEO/R process.

These and other objects of this invention are addressed by an apparatus for concentration and deactivation of actinide nuclear materials comprising spaced apart electrodes made of a composite material comprising at least one oxide, at least one carbon-containing material and lead, a nuclear waste water stream flowing between the electrodes, and a DC power supply operably connected with the electrodes. One of the electrodes is an anode electrode and the other electrode is a cathode electrode. Upon application of a voltage between the two electrodes, nuclear cations are electrosorbed toward the anode electrode and entrained in the metal oxide surface. The electric field promotes both the adsorption process and the desorption release. The apparatus has not only ion-exchange functions, but also adsorbent functions and electrocapacitive deionization functions. If the potential increases, the electrochemical cell oxidizes or reduces the nuclear waste, thereby reducing the radioactivity.

The objects of this invention are also addressed by a method for concentration and deactivation of actinide nuclear waste materials in which a voltage is applied to a spaced apart pair of electrodes made of a composite material comprising at least one oxide, a carbon-containing material and lead, and the electrodes are contacted with a nuclear waste water stream, whereby nuclear cations in the nuclear waste water stream are attracted to one of the electrodes and anions in the nuclear waste water stream are attracted to the other of the electrodes, forming substantially deionized water and a concentrated nuclear waste material. Reversing the polarity enables nuclear cation release from the one electrode, i.e. the anode electrode.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
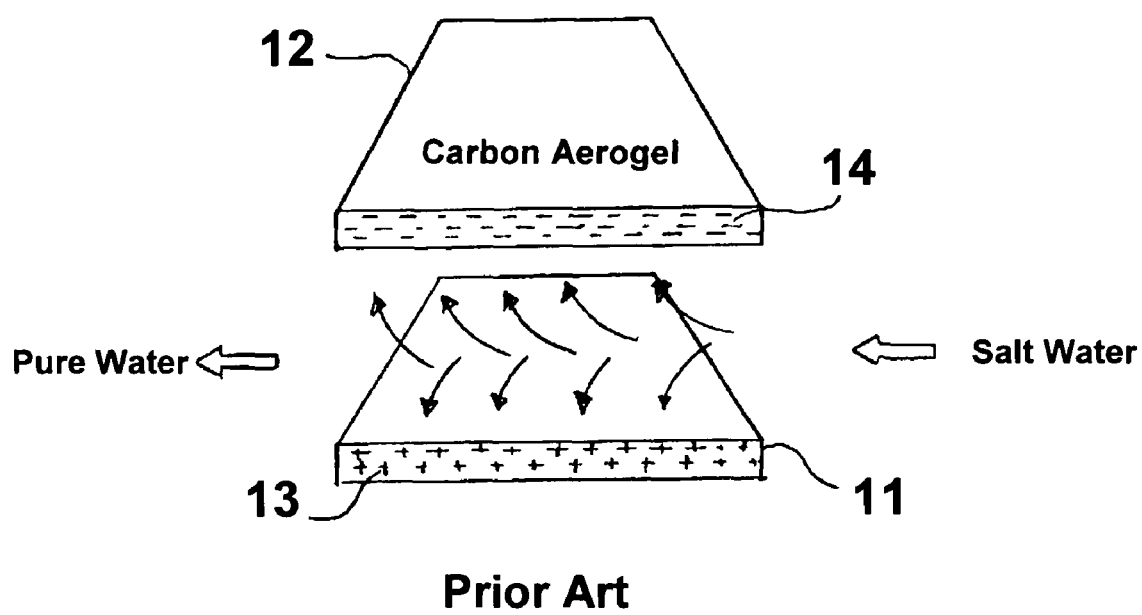
FIG. 1 is a diagram depicting a conventional capacitive deionization method.
Figure 2:
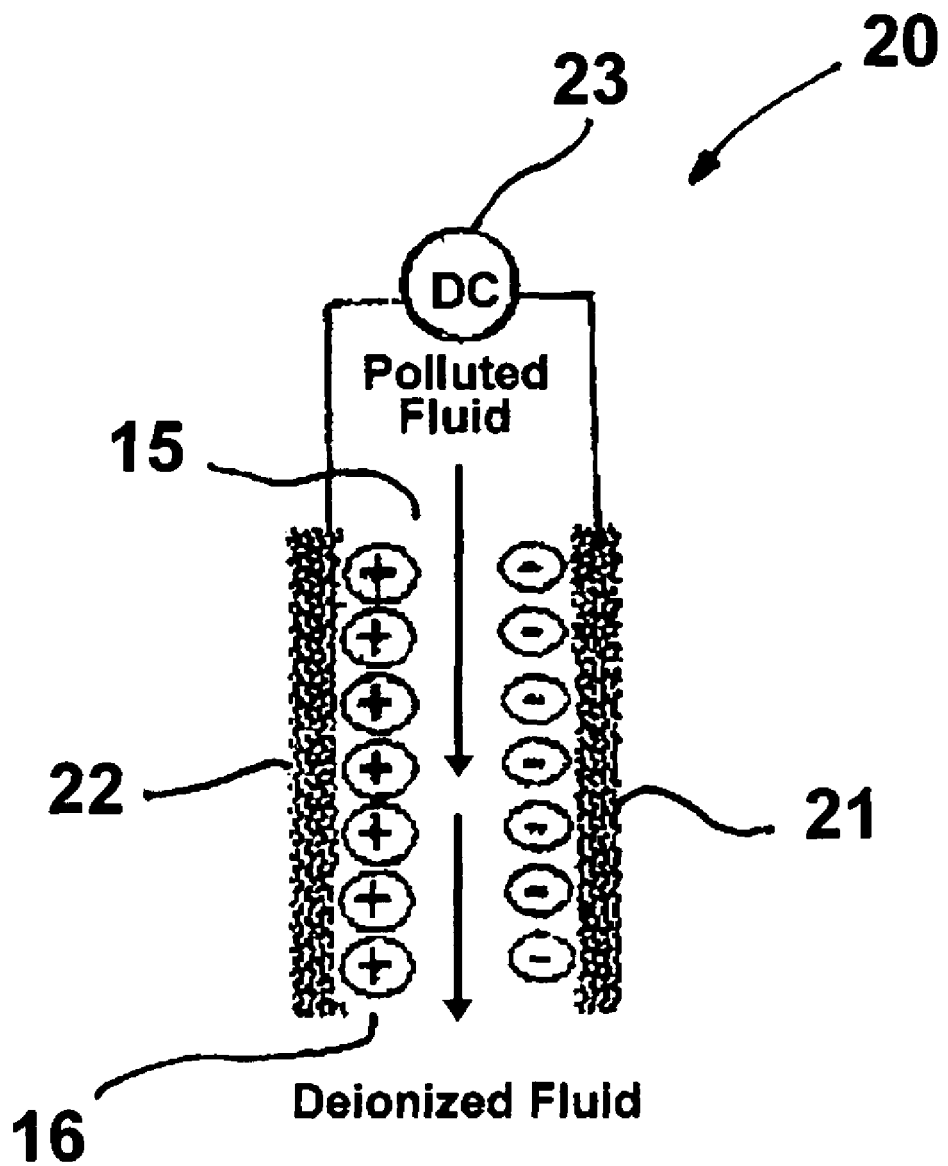
FIG. 2 is a diagram showing a simplified apparatus for continuous nuclear waste concentration with oxide/graphite/resin composite electrodes in accordance with one embodiment of this invention.
Figure 4:
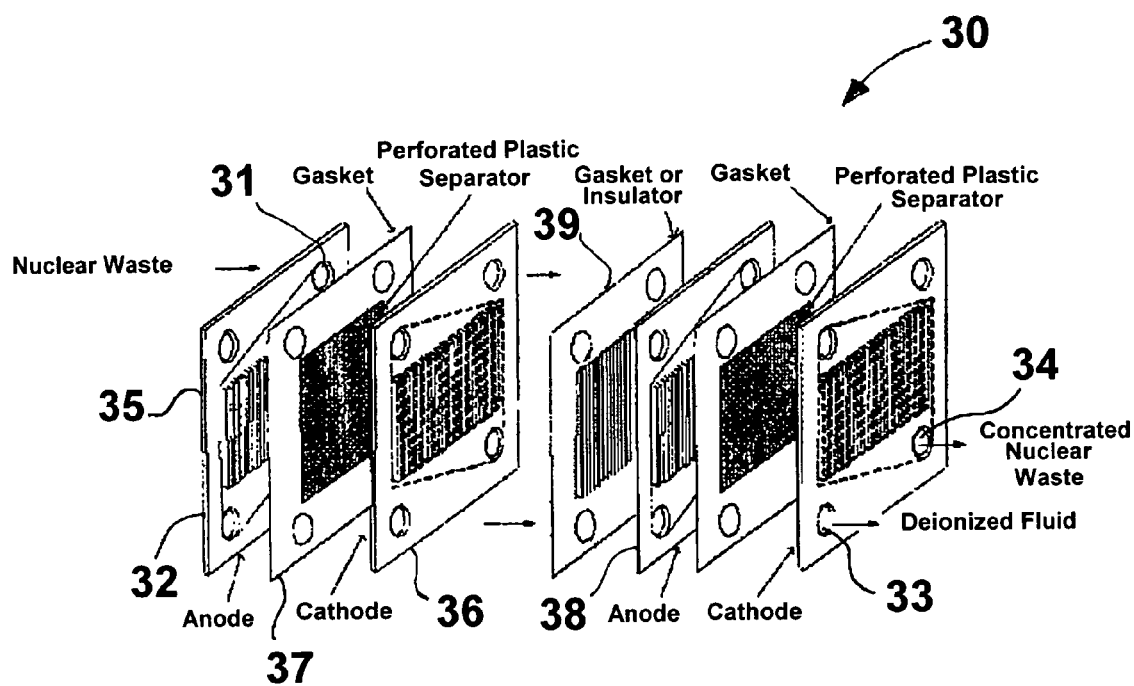
FIG. 4 is a schematic diagram showing an exploded view of a capacitive deionization stack for nuclear waste and water treatment in accordance with one embodiment of this invention.

The invention described and claimed herein is an apparatus and method for continuous nuclear wastes volume reduction and stabilization. The basic component of the apparatus is a single electrochemical cell unit 20, as shown in FIG. 2, comprising a pair of spaced apart electrodes 21, 22, a DC power supply 23 operably connected with the electrodes, and a nuclear waste water stream flowing between the electrodes. In accordance with one embodiment of this invention, a plurality of electrochemical cell units 20 are assembled to form an electrochemical cell stack 30, as shown in FIG. 4.

FIG. 2 shows the basic concept of the method of this invention. As shown therein, a polluted fluid, containing nuclear wastes, is introduced into the top 15 of a cell 20 having electrodes 21, 22. The outlet 16 of the cell can be controlled to enable operation at different pressures as needed. Electrical voltage is added on the cell with the potential scale depending upon the contaminants in the fluid. As the fluid flows through the cell, cations (positive charges) in the fluid are attracted to the anode electrode 22 and anions (negative charges) in the fluid are attracted to the cathode electrode 21. The fluid flowing out the bottom of the cell is, thus, a substantially deionized fluid. Temperatures at which the method of this invention may be carried out are less than or equal to about 100° C., preferably in the range of about room temperature to about 100° C. This is compared to conventional processes which are carried out at higher temperatures. Pulse charge/discharge intervals may be controlled for different time periods and at different voltages. Reversing the polarity enables nuclear cation release from the anode electrode. For example, if the concentration of the nuclear waste is relatively low, the adsorption time required for these wastes is longer.

In accordance with one embodiment of this invention, the actinide solids or substrate-supported species, such as incinerator ash, sand/slag/crucible, and combustibles, are dissolved in a dilute nitric acid solution, e.g. in the range of about 0.1 to about 6M nitric acid. The resulting solution comprises actinium nitrate and other radioactive nitrates, e.g. $Eu(NO_3)_3$, $UO_2(NO_3)_2$. Using NaOH, the solution can be adjusted to a pH in the range of about 2 to about 6.

The electrodes employed in the cell unit of this invention are made from a composite material comprising at least one oxide, a carbon-containing material, lead and a resin. In accordance with one embodiment of this invention, the electrodes comprise in a range of about 5-10 wt. % oxide, about 5-10 wt. % lead, and about 5-10 wt. % resin, with the balance being a carbon-containing material, such as graphite. In accordance with one particularly preferred embodiment of this invention, the composite material comprises at least one metal oxide, silica, a carbon-containing material, metal lead, and a resin. These electrode components are preferably uniformly distributed throughout the electrodes. The oxides in the electrodes function to attract nuclear cations and the carbon in the electrodes provides electrical conductivity. In accordance with one embodiment of this invention, the electrodes comprise metal lead powders which, upon contact with the nuclear waste water stream, are oxidized to form lead oxide, which attracts nuclear cations.

The electrodes may be produced in accordance with any means known to those skilled in the art. In one preferred method, the electrodes are molded using a mixture of the metal oxides, silica, carbon-containing material, e.g. carbon or graphite powders, and resin. Particle sizes in the mixture are preferably less than about 15 microns. The porosity of the resulting electrodes in accordance with one embodiment of this invention is preferably in the range of about 5 to about 60 volume percent of the electrodes. The resins are cross-linked and stable. Thus, if they lose their efficacy for binding due to radiation damage from the adsorbed actinide elements, the electrodes will still retain mechanical strength due to the high pressure compression and high temperature treatment of the molding process.

Typical molding pressures for molding of the electrodes is in the range of about 3000-5000 psi with molding temperatures in the range of about 350° F. to about 450° F. Pressure is applied to the blend for about 1 to about 5 minutes. In accordance with one preferred embodiment, the molding dies are provided with straight channel features so that the channels of the first die are perpendicular to those of the second die when the mold is closed. Only enough composite powder is loaded into the dies so that the opposing metal dies are prevented from touching during compression. Following removal of the electrode from the mold, a clean-up operation such as liquid honing may be desirable to increase surface area and remove mold release agents.

Figure 3:
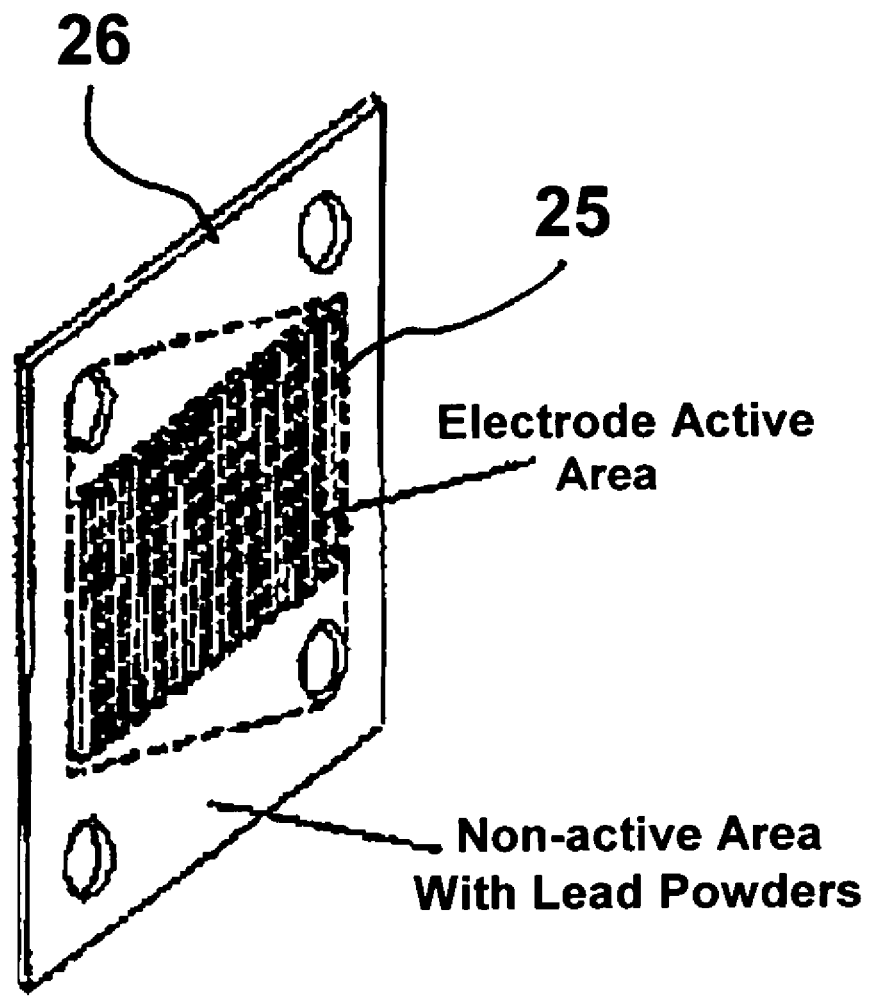
FIG. 3 is a schematic diagram of an electrode plate for an apparatus for concentrating and deactivating actinides in accordance with one embodiment of this invention.

In accordance with one embodiment of this invention as shown in FIG. 3, the electrodes of the electrochemical cell are substantially planar and have a centrally disposed electrode active area 25 and a peripheral area 26 around the centrally active area that is electrode inactive. To differentiate between the centrally disposed electrode active region 25 and the peripheral non-active area 26 of the electrodes, the porosity of the centrally disposed electrode active area is substantially greater than the porosity of the peripheral non-active area. In accordance with one embodiment of this invention, the peripheral non-active area is dense, that is, substantially non-porous. In accordance with this embodiment, the lead powders are oxidized to form lead oxide in the centrally disposed electrode active area 25 after contact with the nuclear waste water stream and the lead powders in the non-active peripheral areas 26 remain in the metal phase so as to prevent the emission of radioactivity to the environment surrounding the cell. Thus, the lead in the electrodes performs two functions—attracting nuclear waste and preventing or reducing radioactive emissions. Compared to the gel-carbon electrodes of the conventional CDI system, the oxide, mixed graphite or carbon and lead composite of the electrodes of this invention have lower corrosion rates.

In accordance with one preferred embodiment of this invention, the electrodes are substantially planar in shape as shown in FIG. 3. The electrodes and separators may be formed into a stack 30 for nuclear waste treatment as shown in FIG. 4. Stack 30 comprises a plurality of electrochemical cell units, each said unit comprising an anode electrode 35, a cathode electrode 36, and a porous insulator 37 disposed between the anode and cathode electrodes. A gasket 39 is also disposed between cathode electrode 36 of one electrochemical cell unit and anode electrode 38 of an adjacent electrochemical cell unit in the stack. In accordance with one embodiment of this invention, the porous insulators are made of polyethylene or polypropylene. The substantially planar electrodes and gaskets/insulators form a plurality of aligned perforations, thereby providing conduits within the stack for transmission of the nuclear waste stream and the deionized fluid stream through the stack.

Sealing along the cell perimeter is provided by a peripheral gasket disposed between the anode and cathode electrodes of each electrochemical cell unit and between adjacent cell units. To prevent shorting between the conductive nuclear waste water stream and the conductive electrodes, the non-active areas of the electrodes are coated with an insulating material, such as TEFLON® (polytetrafluoroethylene).

The nuclear waste water stream is introduced into the stack 30 through waste stream inlet 31. When voltage is applied to the stack, the nuclear waste cations are adsorbed on the anode electrode 32 and entrained on the metal oxide surface. The remaining deionized fluid includes sand, ash and water, all of which are discharged from the stack through deionized water outlet 33. When discharging the concentrated nuclear waste, the deionized water outlet 33 is blocked and the concentrated nuclear waste is discharged through concentrated nuclear waste outlet 34. Thus, the process is continuous. The fluid may be monitored by a mercury drop electrode Model 303A from Princeton Applied Research Corporation with a potentiostat Model 263.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for concentration and deactivation of actinide nuclear waste materials comprising the steps of:

applying a voltage to a spaced apart pair of porous electrodes, said porous electrodes made of a composite material comprising at least one oxide, a carbon-containing material and lead substantially uniformly distributed throughout said electrodes and having a centrally disposed electrode active region and a peripheral electrode non-active region; and passing a nuclear waste water stream through the pores of said porous electrodes, whereby nuclear cations in said nuclear waste water stream are attracted to one of said electrodes and anions in said nuclear waste water stream are attracted to the other of said electrodes, forming a substantially deionized water stream and a concentrated nuclear waste material.

2. A method in accordance with claim 1, wherein said nuclear waste water stream has a temperature one of less than and substantially equal to about 100° C.

3. A method in accordance with claim 1, wherein said nuclear waste water stream is produced by dissolving actinide-containing solids in an aqueous solvent.

4. A method in accordance with claim 3, wherein said aqueous solvent is a nitric acid solution.

5. A method in accordance with claim 1, wherein said nuclear waste water stream has a pH in a range of about 2 to about 6.

6. A method in accordance with claim 1, wherein said at least one oxide is a metal oxide.

7. A method in accordance with claim 6, wherein said composite material further comprises silica.

* * * * *